United States Patent [19]

Tieman

[11] 4,033,952
[45] July 5, 1977

[54] 1,1,1-TRICHLORO-3-NITRO-3-(TETRAHYDRO-2H-1,3-THIAZIN-2-YLIDENE)-2-PROPANONE

[75] Inventor: Charles H. Tieman, Modesto, Calif.

[73] Assignee: Shell Oil Company, Houston, Tex.

[22] Filed: July 19, 1976

[21] Appl. No.: 706,312

[52] U.S. Cl. .............................. 260/243 R; 424/246
[51] Int. Cl.$^2$ ...................................... C07D 279/06

[58] Field of Search ................................ 260/243 R

[56] References Cited
UNITED STATES PATENTS 3,962,225  6/1976  Powell ............................... 260/243

*Primary Examiner*—John M. Ford

[57] ABSTRACT

The title compound, useful as an insecticide.

1 Claim, No Drawings

1,1,1-TRICHLORO-3-NITRO-3-(TETRAHYDRO-2H-1,3-THIAZIN-2-YLIDENE)-2-PROPANONE

DESCRIPTION OF THE INVENTION

It has been found that useful insecticidal activity is possessed by 1,1,1-trichloro-3-nitro-3-(tetrahydro-2H-1,3-thiazin-2-ylidene)-2-propanone, said ketone having the formula:

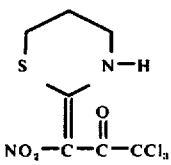

This ketone is a resonance hybrid, the principal forms contributing thereto being described by the formulae:

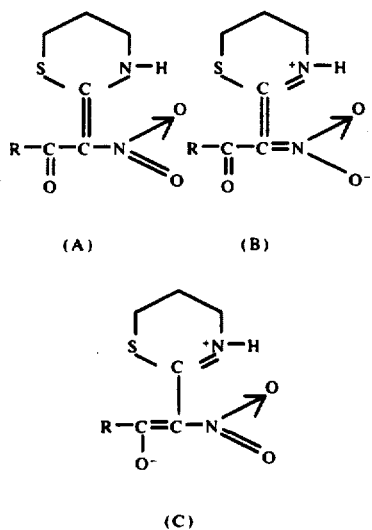

wherein R is the CCl₃ moiety.

Form A is designated as nitro(tetrahydro-2H-1,3-thiazin-2-ylidene)methyl trichloromethyl ketone, Form B as 2-(trichloroacetylcarbonyl-aci-nitromethyl)-5,6-dihydro-4H-1,3-thiazinium hydroxide inner salt, and Form C as 2-(3,3,3-trichloro-2-hydroxy-1-nitro-1-propenyl)-5,6-dihydro-4H-1,3-thiazinium hydroxide inner salt.

This compound may also exist in the corresponding tautomeric enol form which can be described by the formula:

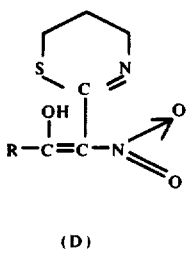

This form (Form D) can be designated as a 2-nitro-2-(5,6-dihydro-2H-1,3-thiazin-2-yl) derivative of the unsaturated alcohol, —CH₂=C(OH)—R.

The resonance hybrid may exist as either of two geometric (cis-trans) isomers, depending upon the spatial relationship of the moieties about the bond between the carbon atom of the nitromethylene moiety and the ring carbon atom to which it is joined.

In this specification, for the sake of simplicity, the compound will be referred to as 1,1,1-trichloro-3-nitro-3-(tetrahydro-2H-1,3-thiazin-2-ylidene)-2-propanone. This terminology is intended to include all of the contributors to the resonance hybrid, the geometric isomers, and the enol form, as well as mixtures thereof.

The compound of the invention (referred to hereinafter as Compound 1) can be prepared as follows (in this example, the identities of the precursors and of the final product were confirmed by appropriate elemental and spectral analyses):

To a mixture of 235 g of 5,6-dihydro-2-methylthio)-4H-1,3-thiazine (A.F. McKay et al., J. Am. Chem. Soc., 80, 3339 (1958)) and 2 g of zinc chloride at approximately 115° in a nitrogen atmosphere, 263 g of ethyl nitroacetate (S. Zen, et al., Kogyo Kagaku Zasshi, 74, 70 (1971)) was added dropwise over a 1.5 hour period. The mixture was held at 110°-120°. When evolution of methyl mercaptan ceased after 45 minutes further stirring of the heated mixture, 1 g of zinc chloride was added and the mixture was stirred at about 115° for 1.25 hours. An additional 1 g of zinc chloride then was added and stirring of the mixture at about 115° was continued for 1.5 hours. The mixture then was poured into a cooled solution of 2/1 (volume) ether/isopropyl alcohol mixture. The crystallized product was collected, washed with ether and dried under reduced pressure to leave a tan solid, m.p. 100°-102°, which on recrystallization from methanol gave ethyl nitro(tetrahydro-2H-1,3-thiazin-2-ylidene)acetate (1A) as a pale yellow solid, m.p. 105°-106°.

2.3 g of 1A was added to 10 ml of 20% aqueous sodium hydroxide and the mixture was stirred at room temperature for 12 hours. The resulting solution was treated dropwise with 3.5 g of acetic acid. The addition was accompanied by vigorous gas evolution. The resulting mixture was extracted with methylene chloride and the extract was dried (magnesium sulfate) and concentrated under reduced pressure to give tetrahydro-2-(nitromethylene)-2H-1,3-thiazine (1B) as a pale yellow solid, m.p. 76°-78°.

A mixture of 160 g of 1B, prepared as described above, 150 ml of chloral and 1 liter of methylene chloride was refluxed for 1.5 hours, cooled in ice, and treated with 150 ml of acetic anhydride and then with 150 ml of triethylamine added over a 20-minute period. The next day, the mixture was washed successively with water, 3N hydrochloric acid and sodium bicarbonate solution. Then the methylene chloride solution was dried (MgSO₄) and the solvent was evaporated. The remaining oil was diluted with methanol and the resulting product was filtered. Recrystallization of the solid product from ethyl acetate gave Compound 1, as a yellow solid, m.p.: 139° C (with decomposition).

The compound of this invention exhibits useful insecticidal activity, being of particular interest for control of the larval "caterpillar" or "worm" forms of lepidopterous insects of the genus Heliothis, such as *H. zea* (corn earworm, cotton bollworm, tomato fruitworm), *H. virescens* (tobacco budworm); the genus Agrotis, such as *A. ipsilon* (black cutworm); the genus Trichoplusia, such as *T. ni* (cabbage looper), and the genus Spodoptera, such as *S. littoralis* (Egyptian cotton leafworm).

The activity of Compound 1 with respect to insects was determined by using standardized test methods to establish the $LC_{50}$ dosage (in milligrams of test compound per 100 milliliters of solvent or liquid carrier required in the solution or suspension of test compound used) that was required to kill 50% of the test insects. The test insects were the housefly, corn earworm, pea aphid and 2-spotted spider mite. Activity with respect to mosquito larvae was determined by placing the larvae in water containing the test compound.

Compound 1 was found to be inactive with respect to the mites and slightly active with respect to mosquito larvae. It was active with respect to the pea aphids, very active with respect to the houseflies and was highly active with respect to the corn earworms. In the course of the tests it was noted that Compound 1 acted very quickly on all of the insects.

The invention includes within its scope insecticidal compositions comprising an adjuvant — that is, a carrier, optionally a surface-active agent — and, as active ingredient, the insecticide of this invention. Likewise the invention includes also a method of combatting insect pests at a locus which comprises applying to the locus an effective amount of the insecticide of the invention.

The term "carrier" as used herein means a material which may be inorganic or organic and of synthetic or natural origin with which the active compound is mixed or formulated to facilitate its application to the plant, seed, soil or other object to be treated, or its storage, transport or handling. The carrier may be a solid or a liquid.

Suitable solid carriers may be natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements such as for example, carbon and sulfur; natural and synthetic resins such as, for example, coumarone resins, polyvinyl chloride and styrene polymers and copolymers; solid polychlorophenols; bitumen, waxes such as beeswax, paraffin wax, and chlorinated mineral waxes; degradable organic solids, such as ground corn cobs and walnut shells; and solid fertilizers, for example, super-phosphates.

Suitable liquid carriers include solvents for the salts of this invention and liquids in which the toxicant is insoluble or only slighty soluble.

Examples of such solvents and liquid carriers generally are water, alcohols, for example, isopropyl alcohol; ketones, such as acetone, methyl ethyl ketone, methyl isobutyl ketone and cyclohexanone; ethers; aromatic hydrocarbons such as benzene, toluene and xylene; petroleum fractions, such as kerosene, light mineral oils; chlorinated hydrocarbons, such as carbon tetrachloride, perchlorethylene, trichloroethane; including liquefied normally vaporous gaseous compounds. Mixtures of different liquids are often suitable.

If used, the surface-active agent may be an emulsifying agent or a dispersing agent or a wetting agent. It may be nonionic or ionic. Surface-active agents usually applied in formulating pesticides may be used. Examples of such surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; fatty acid salts of low molecular weight, mono-, di- and trialkyl- amines; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates or these condensation products; alkali or alkaline earth metal salts, preferably sodium salts, of sulfuric or sulfonic acids esters containing at least 10 carbon atoms in the molecule, for example, sodium lauryl sulfate, sodium secondary alkyl sulfates, sodium salts of sulfonated caster oil, and sodium alkylaryl sulfonates such as sodium dodecylbenzene sulfonate; and polymers of ethylene oxide and copolymers of ethylene oxide and propylene oxide.

The compositions of the invention may be formulated as wettable powders, dusts, granules, solutions, emulsifiable concentrates, emulsions, suspension concentrates or aerosols. Encapsulated formulations and controlled release formulations also are contemplated, as are bait formulations. Wettable powders are usually compounded to contain 25, 50 or 75%w of toxicant and usually contain, in addition to solid carrier, 3–10%w of stablilizer(s) and/or other additives such as penetrants or stickers. Dusts are usually formulated as a dust concentrate having a similar composition to that of a wettable powder but without a dispersant, and are diluted in the field with further solid carrier to give a composition usually containing ½–10%w of active ingredient. Granules may be manufactured by agglomeration or impregnation techniques. Generally, granules will contain ½–25%w active ingredient and 0–10%w of additives such as stabilizers, slow release modifiers and binding agents. Emulsifiable concentrates usually contain, in addition to the solvent, and when necessary, co-solvent, 10–50%w/v active ingredient, 2–20%w/v emulsifiers and 0–20%w/v of appropriate additives such as stabilizers, penetrants and corrosion inhibitors. Suspension concentrates are compounded so as to obtain a stable, non-sedimenting, flowable product and usually contain 10–75%w active ingredient, 0–5%w of dispersing agents, 0.1–10%w of suspending agents such as protective colloids and thixotropic agents, 0–10%w of appropriate additives such as defoamers, corrosion inhibitors, stabilizers, penetrants and stickers, and as carrier, water or an organic liquid in which the active ingredient is substantially insoluble; certain organic additives or inorganic salts may be dissolved in the carrier to assist in preventing sedimentation or as antifreeze agents for water.

Aqueous dispersions and emulsions, for example, compositions obtained by diluting a wettable powder or an emulsifiable concentrate according to the invention with water, also lie within the scope of the present invention.

The compositions of the invention may also contain other ingredients, for example, other compounds possessing pesticidal, herbicidal or fungicidal properties, or attractants, such as pheromones, attractive food ingredients, and the like, for use in baits and trap formulations.

These compositions are applied in sufficient amount to supply the effective dosage of active ingredient at the locus to be protected. This dosage is dependent upon many factors, including the carrier employed, the method and conditions of application, whether the formulation is present at the locus in the form of an aerosol, or as a film, or as discrete particles, the thickness of film or size of particles, the insect species to be controlled and the like, proper consideration and resolution of these factors to provide the necessary dosage of the active ingredient at the locus being within the skill of those versed in the art. In general, however, the effective dosage of salts of this invention at the locus to be protected — i.e., the dosage to which the insect contacts — is of the order of 0.001% to 0.5% based on the total weight of the formulation, though under some circumstances the effective concentration will be as little as 0.001% or as much as 2%, on the same basis.

I claim as my invention:

1. A resonance hybrid in which the significant forms which contribute thereto are represented by the formla

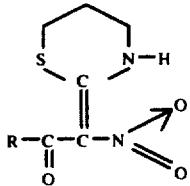

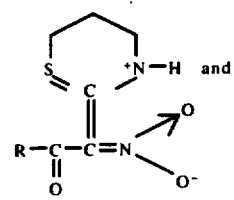 and

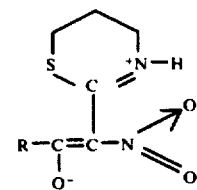

and including the enol form represented by the formula

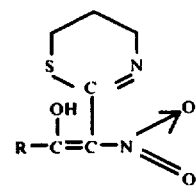

wherein R is trichloromethyl.

* * * * *